US009120078B2

(12) United States Patent
Chewter et al.

(10) Patent No.: US 9,120,078 B2
(45) Date of Patent: Sep. 1, 2015

(54) PROCESS FOR THE PREPARATION OF AN OLEFINIC PRODUCT, OXYGENATE CONVERSION CATALYST PARTICLES, AND PROCESS FOR THE MANUFACUTRE THEREOF

(75) Inventors: Leslie Andrew Chewter, Amsterdam (NL); Jeroen Van Westrenen, Amsterdam (NL); Ferry Winter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 643 days.

(21) Appl. No.: 13/141,014

(22) PCT Filed: Dec. 21, 2009

(86) PCT No.: PCT/EP2009/067645
§ 371 (c)(1),
(2), (4) Date: Aug. 24, 2011

(87) PCT Pub. No.: WO2010/072716
PCT Pub. Date: Jul. 1, 2010

(65) Prior Publication Data
US 2011/0313225 A1    Dec. 22, 2011

(30) Foreign Application Priority Data

Dec. 22, 2008 (EP) .................................. 08172565

(51) Int. Cl.
| C07C 1/20 | (2006.01) |
| B01J 29/06 | (2006.01) |
| B01J 29/80 | (2006.01) |
| B01J 37/34 | (2006.01) |
| C10G 3/00 | (2006.01) |
| B01J 29/40 | (2006.01) |
| B01J 29/70 | (2006.01) |
| B01J 37/00 | (2006.01) |

(52) U.S. Cl.
CPC ............... *B01J 29/061* (2013.01); *B01J 29/80* (2013.01); *B01J 37/346* (2013.01); *C07C 1/20* (2013.01); *C10G 3/44* (2013.01); *C10G 3/49* (2013.01); *B01J 29/40* (2013.01); *B01J 29/70* (2013.01); *B01J 37/0045* (2013.01); *B01J 2229/20* (2013.01); *B01J 2229/42* (2013.01); *C07C 2521/16* (2013.01); *C07C 2529/70* (2013.01); *C07C 2529/80* (2013.01); *C10G 2300/1088* (2013.01); *C10G 2400/02* (2013.01); *C10G 2400/20* (2013.01); *C10G 2400/22* (2013.01)

(58) Field of Classification Search
USPC ....................................... 585/639–642; 502/67
See application file for complete search history.

(56) References Cited

U.S. PATENT DOCUMENTS

| 4,076,842 | A | 2/1978 | Plank et al. ..................... 423/328 |
| 4,397,827 | A | 8/1983 | Chu |
| 4,556,477 | A | 12/1985 | Dwyer ........................... 208/111 |
| 4,579,994 | A | 4/1986 | Kiyozumi et al. ............. 585/640 |
| 4,665,268 | A * | 5/1987 | Lee et al. ........................ 585/640 |
| 4,929,338 | A | 5/1990 | Wormsbecher ................ 208/120 |
| 5,002,653 | A | 3/1991 | Kennedy et al. .............. 208/118 |
| 6,046,373 | A | 4/2000 | Sun .................................. 85/640 |
| 6,797,851 | B2 * | 9/2004 | Martens et al. ................ 585/640 |
| 2002/0183192 | A1 * | 12/2002 | Verduijn et al. ................. 502/67 |

FOREIGN PATENT DOCUMENTS

| DE | 10043644 | 3/2002 | ............. C07C 67/02 |
| WO | WO2004071656 | 8/2004 | ............. B01J 35/00 |
| WO | WO2007135052 | 11/2007 | ............. C07C 2/86 |

OTHER PUBLICATIONS

Baerlocher, Ch., et al.; Database of Zeolite Structures; http://www.iza-structure.org/databases May 4, 2010.
Weissermel, Klaus et al; Industrial Organic Chemistry, 2. Basic Products of Industrial Syntheses; $3^{rd}$ Edition; pp. 1-58; 1997.

* cited by examiner

*Primary Examiner* — In Suk Bullock
*Assistant Examiner* — Sharon Pregler

(57) ABSTRACT

The invention provides a process for the preparation of an olefinic product, the process comprising reacting an oxygenate feedstock in the presence of formulated oxygenate conversion catalyst particles to produce the olefinic product, the formulated catalyst particles comprising a combination of at least a molecular sieve having one-dimensional 10-membered ring channels and a matrix wherein a Group II metal species has been added to the catalyst particles after the combination of said molecular sieve and the matrix. Further a process for the manufacture of formulated oxygenate conversion catalyst particles, comprising combining of at least a molecular sieve having one-dimensional 10-membered ring channels and a matrix to form catalyst particles, and adding a Group II metal species to the catalyst particles after the combination of said molecular sieve and the matrix; and also oxygenate conversion catalyst particles comprising a combination of at least a molecular sieve having one-dimensional 10-membered ring channels, a further molecular sieve having more-dimensional channels, a matrix, and a Group II metal species.

7 Claims, No Drawings

PROCESS FOR THE PREPARATION OF AN OLEFINIC PRODUCT, OXYGENATE CONVERSION CATALYST PARTICLES, AND PROCESS FOR THE MANUFACUTRE THEREOF

PRIORITY CLAIM

The present application claims priority from PCT/EP2009/067645, filed 21 Dec. 2009, which claims priority from European Application 08172565.7, filed 22 Dec. 2008.

BACKGROUND

This invention relates to a process for the preparation of an olefinic product, to oxygenate conversion catalyst particles, and to a process for the manufacture of formulated oxygenate conversion particles.

Processes for the preparation of olefins from oxygenates are known in the art. Of particular interest is often the production of light olefins, in particular ethylene and/or propylene. The oxygenate feedstock can for example comprise methanol and/or dimethylether, and an interesting route includes their production from synthesis gas derived from e.g. natural gas or via coal gasification.

For example, WO2007/135052 discloses a process wherein an alcohol and/or ether containing oxygenate feedstock and an olefinic co-feed are reacted in the presence of a zeolite having one-dimensional 10-membered ring channels to prepare an olefinic reaction mixture, and wherein part of the obtained olefinic reaction mixture is recycled as olefinic co-feed. With a methanol and/or dimethylether containing feedstock, and an olefinic co-feed comprising C4 and/or C5 olefins, an olefinic product rich in light olefins can be obtained.

In the known processes a significant amount of coke-precursors such as aromatics are produced. These foul or coke the catalyst, blocking active sites and reducing catalyst activity.

U.S. Pat. No. 4,579,994 discloses the treatment of pure ZSM-5 zeolite to incorporate therein a calcium-containing compound and a phosphorous-containing compound in a conversion reaction of methanol to olefins. This disclosure teaches to treat the zeolite as such, and mentions that the treated zeolite catalyst can be mixed with a carrier such as clay, kaolin and alumina. This is not useful method for manufacturing spray-dried catalyst particles having good attrition resistance using a silica binder. Such spray-dried particles are prepared by mixing a molecular sieve component with, inter alia, a silica binder, and requires an ion exchange after spray drying to remove the alkaline used for the preparation of the binder from the catalyst. Therefore, calcium and phosphorous previously incorporated in the zeolite may fully or partially be lost during this ion exchange.

U.S. Pat. No. 6,046,373 discloses the modification of a SAPO-34 type molecular sieve and zeolites ZSM-5 and ZSM-34, by treating with an alkaline earth metal modifying agent while applying electromagnetic energy at an effective power and frequency. Various other molecular sieves including ZSM-22 are generally mentioned, none of the examples disclose a molecular sieve having one-dimensional 10-membered ring channels. Of the examples given, Example IV, including ZSM-34 (which is an intergrowth of structure types OFF and ERI, OFF having 12- and 8-membered ring channels, and ERI having three-dimensional 8-ring channels) has poor performance in terms of methanol conversion and total $C_2^=$ to $C_4^=$ selectivity compared to the other examples. The example provided with the poorest performance (Example V) uses ZSM-5 having an MFI type structure as the molecular sieve.

There is a need for an improved and efficient oxygenate-to-olefins process wherein a minimum of by-products is formed.

SUMMARY OF THE INVENTION

According to a first aspect of the present invention there is provided a process for the preparation of an olefinic product, the process comprising reacting an oxygenate feedstock in the presence of formulated oxygenate conversion catalyst particles to produce the olefinic product, the formulated catalyst particles comprising a combination of at least a molecular sieve having one-dimensional 10-membered ring channels and a matrix wherein a Group II metal species has been added to the catalyst particles after the combination of said molecular sieve and the matrix.

Applicants have found that by adding Group II metal species in a post-treatment step, i.e. adding to a formulated catalyst comprising a molecular sieve having one-dimensional 10-membered ring channels produces an oxygenate conversion catalyst with improved properties such that beneficial results may be obtained. In particular, the formation of aromatic and saturated by-products in the conversion oxygenate to olefins was found to decrease. As a further advantage, the stability of the catalyst on stream was found to increase.

According to a further aspect of the present invention, there is provided oxygenate conversion catalyst particles comprising a combination of at least a molecular sieve having one-dimensional 10-membered ring channels, a further molecular sieve having more-dimensional channels, a matrix, and a Group II metal species. The Group II metal species is preferably present in an amount of 0.05-10 wt % based on the weight of catalyst particles. Further, the weight ratio between the molecular sieve having one-dimensional 10-membered ring channels and the further molecular sieve having more-dimensional channels is preferably in the range of 1:1 to 100:1.

DETAILED DESCRIPTION OF THE INVENTION

The Group II species may be present on an acidic sites of the molecular sieve or may be in a compound, for example where the Group II species is calcium it may be present as calcium phosphate or calcium oxide.

The external surface area of the catalyst particles is normally 1-500m$^2$/g, preferably 40-200 m$^2$/g. "External surface area" as used herein refers to the total surface area of the molecular sieve excluding the surface area of micropores. Micropores are defined herein as pores with widths not exceeding 2.0 nm.

The group II species may be present in an amount of from 0.05-10 wt % of the overall catalyst, preferably 0.05-5 wt %, more preferably 0.2-2.5 wt %, especially 1-2 wt %.

Preferably the Group II metal species comprises a metal selected from the group consisting of magnesium, calcium, strontium and barium; especially calcium. The metal can be present in any form, e.g. ionic or bound.

The process to prepare an olefin is carried out in presence of a molecular sieve having one-dimensional 10-membered ring channels. These are understood to be molecular sieves having only 10-membered ring channels in one direction which are not intersected by other 8, 10 or 12-membered ring channels from another direction.

Preferably, the molecular sieve is selected from the group of TON-type (for example zeolite ZSM-22), MTT-type (for example zeolite ZSM-23), STF-type (for example SSZ-35), SFF-type (for example SSZ-44), EUO-type (for example ZSM-50), and EU-2-type molecular sieves or mixtures thereof.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type molecular sieves are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type molecular sieves are more particularly described in e.g. U.S. Pat. No. 4,397,827. For purposes of the present invention, EU-2 is considered to include its isotypes, e.g., ZSM-48.

In a further preferred embodiment a molecular sieve of the MTT-type, such as ZSM-23, and/or a TON-type, such as ZSM-22 is used.

Molecular sieve and zeolite types are for example defined in Ch. Baerlocher and L. B. McCusker, Database of Zeolite Structures: http://www.izastructure.org/databases/, which database was designed and implemented on behalf of the Structure Commission of the International Zeolite Association (IZA-SC), and based on the data of the 4th edition of the Atlas of Zeolite Structure Types (W. M. Meier, D. H. Olson and Ch. Baerlocher). The Atlas of Zeolite Framework Types, 5th revised edition 2001 and 6$^{th}$ edition 2007 may also be consulted.

Preferably, molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. When the molecular sieves are prepared in the presence of organic cations the molecular sieve may be activated by heating in an inert or oxidative atmosphere to remove organic cations, for example, by heating at a temperature over 500° C. for 1 hour or more. The zeolite is typically obtained in the sodium or potassium form. The hydrogen form can then be obtained by an ion exchange procedure with ammonium salts followed by another heat treatment, for example in an inert or oxidative atmosphere at a temperature over 300° C. The molecular sieves obtained after ion-exchange are also referred to as being in the ammonium form.

Preferably the molecular sieve having one-dimensional 10-membered ring channels has a silica to alumina ratio (SAR) in the range from 1 to 500, preferably in the range from 10 to 200. The SAR is defined as the molar ratio of SiO2/Al2O3 corresponding to the composition of the molecular sieve.

For ZSM-22, a SAR in the range of 40-150 is preferred, in particular in the range of 70-120. Good performance in terms of activity and selectivity has been observed with a SAR of about 100.

For ZSM-23, an SAR in the range of 20-120 is preferred, in particular in the range of 30-80. Good performance in terms of activity and selectivity has been observed with a SAR of about 50.

In a special embodiment the reaction is performed in the presence of a more-dimensional molecular sieve, such as ZSM-5. Suitably to this end the oxygenate conversion catalyst comprises at least 1 wt %, based on total molecular sieve in the oxygenate conversion catalyst, of a further molecular sieve having more-dimensional channels, in particular at least 5 wt %, more in particular at least 8 wt %. The further molecular sieve having more-dimensional channels is understood to have intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. The second molecular sieve can be for example a FER type zeolite which is a two-dimensional structure and has 8- and 10-membered rings intersecting each other. Preferably however the intersecting channels in the second molecular sieve are each 10-membered ring channels. Thus the second molecular sieve may be a zeolite, or a SAPO-type (silicoaluminophosphate) molecular sieve. More preferably however the second molecular sieve is a zeolite. A preferred second molecular sieve is an MFI-type zeolite, in particular zeolite ZSM-5.

The presence of the further molecular sieve in the oxygenate conversion catalyst was found to improve stability (slower deactivation during extended runs) and hydrothermal stability compared to a catalyst with only the one-dimensional molecular sieve and without the more-dimensional molecular sieve. Without wishing to be bound by a particular hypothesis or theory, it is presently believed that this is due to the possibility for converting larger molecules by the second molecular sieve having more-dimensional channels, that were produced by the first molecular sieve having one-dimensional 10-membered ring channels, and which would otherwise form coke. When the one-dimensional aluminosilicate and the more-dimensional molecular sieve are formulated such that they are present in the same catalyst particle, such as in a spray-dried particle, this intimate mix was found to improve the selectivity towards ethylene and propylene, more in particular towards ethylene.

The weight ratio between the molecular sieve having one-dimensional 10-membered ring channels, and the further molecular sieve having more-dimensional channels can be in the range of from 1:100 to 100:1. Preferably the further molecular sieve is the minority component, i.e. the above weight ratio is 1:1 to 100:1, more preferably in the range of 9:1 to 2:1.

Preferably the further molecular sieve is an MFI-type molecular sieve, in particular ZSM-5, having a silica to alumina ratio (SAR) of at least 60, more preferably at least 80, even more preferably at least 100, yet more preferably at least 150. At higher SAR the percentage of C4 saturates in the C4 totals produced is minimized. In special embodiments the oxygenate conversion catalyst can comprise less than 35 wt % of the further molecular sieve, based on the total molecular sieve in the oxygenate conversion catalyst, in particular less than 20 wt %, more in particular less than 18 wt %, still more in particular less than 15 wt %.

In one embodiment the oxygenate conversion catalyst can comprise more than 50 wt %, at least 65 wt %, based on total molecular sieve in the oxygenate conversion catalyst, of the molecular sieve having one-dimensional 10-membered ring channels. The presence of a majority of such molecular sieve strongly determines the predominant reaction pathway.

The molecular sieve is used in a formulation, i.e. within the matrix material. For the purposes of this invention 'matrix' is herein defined as including any active matrix component as well as any filler and/or binder. Other components can also be present in the formulation. In a formulation, the molecular sieve in combination with the matrix such as binder and/or filler material is/are referred to as oxygenate conversion catalyst.

It is desirable to provide a catalyst having good mechanical or crush strength, because in an industrial environment the catalyst is often subjected to rough handling, which tends to break down the catalyst into powder-like material. The latter causes problems in the processing. The molecular sieve is therefore incorporated in a binder material. Examples of suitable materials in a formulation include active and inert materials and synthetic or naturally occurring zeolites as well as inorganic materials such as clays, silica, alumina, silica-alumina, titania, zirconia and aluminosilicate. For present purposes, inert materials, such as silica, are preferred because they may prevent unwanted side reactions which may take place in case a more acidic material, such as alumina or silica-alumina is used.

The matrix material may be selected from the group consisting of: silica, magnesia, titania, kaolin, montmorillonite; preferably kaolin. Where kaolin is used, preferably it has less than 3 wt %, preferably less than 1.5 wt % iron, and preferably less than 4 wt %, preferably less than 3 wt % titania; all based on total content of kaolin.

The skilled artisan knows that silica binders can be prepared at low and high pH stabilized by alkaline ($Na^+$), ammonium ($NH_4^+$) and/or by acid ($H^+$). A silica binder that is useful for obtaining spray dried catalyst with good attrition resistance, the binder is stabilized at very low pH (<1.5) or with high alkaline content. High alkaline is preferred, since low pH stabilization may influence the molecular sieve in such environment.

The present invention provides a process for the conversion of oxygenates to olefins as described herein. The oxygenate feedstock comprises oxygenate species having an oxygen-bonded methyl group, such as methanol, dimethylether. Preferably the oxygenate feedstock comprises at least 50 wt % of methanol and/or dimethylether, more preferably at least 80 wt %, most preferably at least 90 wt %.

The oxygenate feedstock can be obtained from a different or separate reactor, which converts methanol at least partially into dimethylether. In this way, water may be removed by distillation and so less water is present in the process of converting oxygenate to olefins, which has advantages for the process design and lowers the severity of hydrothermal conditions the catalyst is exposed to.

The oxygenate feedstock can comprise an amount of water, preferably less than 10 wt %, more preferably less than 5 wt %. Preferably the oxygenate feedstock contains essentially no hydrocarbons other than oxygenates, i.e. less than 5 wt %, preferably less than 1 wt %.

In one embodiment, the oxygenate is obtained as a reaction product of synthesis gas. Synthesis gas can for example be generated from fossil fuels, such as from natural gas or oil, or from the gasification of coal. Suitable processes for this purpose are for example discussed in Industrial Organic Chemistry, Klaus Weissermehl and Hans-Jürgen Arpe, 3rd edition, Wiley, 1997, pages 13-28. This book also describes the manufacture of methanol from synthesis gas on pages 28-30.

In another embodiment the oxygenate is obtained from biomaterials, such as through fermentation. For example by a process as described in DE-A-10043644.

Preferably the oxygenate feedstock is reacted to produce the olefinic product in the presence of an olefinic co-feed. By an olefinic composition or stream, such as an olefinic product, product fraction, fraction, effluent, reaction effluent or the like is understood a composition or stream comprising one or more olefins, unless specifically indicated otherwise. Other species can be present as well. Apart from olefins, the olefinic co-feed may contain other hydrocarbon compounds, such as for example paraffinic compounds. Preferably the olefinic co-feed comprises an olefinic portion of more than 50 wt %, more preferably more than 60 wt %, still more preferably more than 70 wt %, which olefinic portion consists of olefin (s). The olefinic co-feed can also consist essentially of olefin (s).

Any non-olefinic compounds in the olefinic co-feed are preferably paraffinic compounds. Such paraffinic compounds are preferably present in an amount in the range from 0 to 50 wt %, more preferably in the range from 0 to 40 wt %, still more preferably in the range from 0 to 30 wt %.

By an olefin is understood an organic compound containing at least two carbon atoms connected by a double bond. The olefin can be a mono-olefin, having one double bond, or a poly-olefin, having two or more double bonds. Preferably olefins present in the olefinic co-feed are mono-olefins. C4 olefins, also referred to as butenes (1-butene, 2-butene, iso-butene, and/or butadiene), in particular C4 mono-olefins, are preferred components in the olefinic co-feed.

Preferably the olefinic co-feed is at least partially obtained by a recycle stream formed by recycling a suitable fraction of the reaction product comprising C4 olefin. The skilled artisan knows how to obtain such a fractions from the olefinic reaction effluent such as by distillation.

In one embodiment at least 70 wt % of the olefinic co-feed, during normal operation, is formed by the recycle stream, preferably at least 90 wt %, more preferably at least 99 wt %. Most preferably the olefinic co-feed is during normal operation formed by the recycle stream, so that the process converts oxygenate feedstock to predominantly light olefins without the need for an external olefins stream. During normal operation means for example in the course of a continuous operation of the process, for at least 70% of the time on stream. The olefinic co-feed may need to be obtained from an external source, such as from a catalytic cracking unit or from a naphtha cracker, during start-up of the process, when the reaction effluent comprises no or insufficient C4+ olefins.

The C4 fraction resulting from the process according to the invention contains C4 olefin(s), but can also contain a significant amount of other C4 hydrocarbon species, in particular C4 paraffins, because it is difficult to economically separate C4 olefins and paraffins, such as by distillation.

In a preferred embodiment the olefinic co-feed and preferably also the recycle stream comprises C4 olefins and less than 10 wt % of C5+ hydrocarbon species, more preferably at least 50 wt % of C4 olefins, and at least a total of 70 wt % of C4 hydrocarbon species.

The olefinic co-feed and preferably also the recycle stream, can in particular contain at least a total of 90 wt % of C4 hydrocarbon species. In a preferred embodiment, the olefinic co-feed comprises less than 5 wt % of C5+ olefins, preferably less than 2 wt % of C5+ olefins, even more preferably less than 1 wt % of C5+ olefins, and likewise the recycle stream. In another preferred embodiment, the olefinic co-feed, comprises less than 5 wt % of C5+ hydrocarbon species, preferably less than 2 wt % of C5+ hydrocarbon species even more preferably less than 1 wt % of C5+ hydrocarbon species, and likewise the recycle stream.

Thus in certain preferred embodiments, the olefinic portion of the olefinic co-feed, and of the recycle stream, comprises at least 90 wt % of C4 olefins, more preferably at least 99 wt %. Butenes as co-feed have been found to be particularly beneficial for high ethylene selectivity. Therefore one particularly suitable recycle stream consists essentially, i.e. for at least 99 wt %, of 1-butene, 2-butene (cis and trans), isobutene, n-butane, isobutane, butadiene.

In certain embodiments, the recycle stream can also comprise propylene. This may be preferred when a particularly high production of ethylene is desired, so that part or all of the propylene produced is recycled together with C4 olefins.

The preferred molar ratio of oxygenate in the oxygenate feedstock to olefin in the olefinic co-feed depends on the specific oxygenate used and the number of reactive oxygen-bonded alkyl groups therein. Preferably the molar ratio of oxygenate to olefin in the total feed lies in the range of 10:1 to 1:10, more preferably in the range of 5:1 to 1:5 and still more preferably in the range of 3:1 to 1:3.

In a preferred embodiment wherein the oxygenate comprises only one oxygen-bonded methyl group, such as methanol, the molar ratio preferably lies in the range from 5:1 to 1:5 and more preferably in the range of 2.5:1 to 1:2.5.

In another preferred embodiment wherein the oxygenate comprises two oxygen-bonded methyl groups, such as for example dimethylether, the molar ratio preferably lies in the range from 5:2 to 1:10 and more preferably in the range of 2:1 to 1:4. Most preferably the molar ratio in such a case is in the range of 1.5:1 to 1:3.

The process of the present invention can be carried out in a batch, continuous, semi-batch or semi-continuous manner. Preferably the process of the present invention is carried out in a continuous manner.

If the process is carried out in a continuous manner, the process may be started up by using olefins obtained from an external source for the olefinic co-feed, if used. Such olefins may for example be obtained from a steam cracker, a catalytic cracker, alkane dehydrogenation (e.g. propane or butane dehydrogenation). Further, such olefins can be bought from the market.

Typically the oxygenate conversion catalyst deactivates in the course of the process. Conventional catalyst regeneration techniques can be employed, such as burning of coke in a regenerator.

The molecular sieve having one-dimensional 10-membered ring channels used in the process of the present invention can have any shape known to the skilled person to be suitable for this purpose, for it can be present in the form of spray-dried particles, spheres, tablets, rings, extrudates, etc. Extruded catalysts can be applied in various shapes, such as, cylinders and trilobes. Spay-dried particles allowing use in a riser reactor system are preferred.

The reactor system used to produce the olefins may be any reactor known to the skilled person and may for example contain a fixed bed, moving bed, fluidized bed, riser reactor and the like. A riser reactor system is preferred, in particular a riser reactor system comprising a plurality of serially arranged riser reactors.

The reaction to produce the olefins can be carried out over a wide range of temperatures and pressures. Suitably, however, the oxygenate feed and olefinic co-feed are contacted with the molecular sieve at a temperature in the range from 200° C. to 650° C. In a further preferred embodiment the temperature is in the range from 250° C. to 600° C., more preferably in the range from 300° C. to 550° C., most preferably in the range from 450° C. to 550° C. Preferably the reaction to produce the olefins is conducted at a temperature of more than 450° C., preferably at a temperature of 460° C. or higher, more preferably at a temperature of 490° C. or higher. At higher temperatures a higher activity and ethylene selectivity is observed. Molecular sieves having one-dimensional 10-membered ring channels can be operated under oxygenate conversion conditions at such high temperatures with acceptable deactivation due to coking, contrary to molecular sieves with smaller pores or channels, such as 8-membered ring channels. Temperatures referred to hereinabove represent reaction temperatures, and it will be understood that a reaction temperature can be an average of temperatures of various feed streams and the catalyst in the reaction zone.

In addition to the oxygenate, and the olefinic co-feed (when present), a diluent may be fed into the reactor system. It is preferred to operate without a diluent, or with a minimum amount of diluent, such as less than 200 wt % of diluent based on the total amount of oxygenate feed, in particular less than 100 wt %, more in particular less than 20 wt %. Any diluent known by the skilled person to be suitable for such purpose can be used. Such diluent can for example be a paraffinic compound or mixture of compounds. Preferably, however, the diluent is an inert gas. The diluent can be argon, nitrogen, and/or steam. Of these, steam is the most preferred diluent. For example, the oxygenate feed and optionally olefinic co-feed can be diluted with steam, for example in the range from 0.01 to 10 kg steam per kg oxygenate feed.

In one embodiment small amounts of water are added in order to improve the stability of the catalyst by reducing coke formation.

The olefinic product or reaction effluent is typically fractionated. The skilled artisan knows how to separate a mixture of hydrocarbons into various fractions, and how to work up fractions further for desired properties and composition for further use. The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation. It is within the skill of the artisan to determine the correct conditions in a fractionation column to arrive at such a separation. He may choose the correct conditions based on, inter alia, fractionation temperature, pressure, trays, reflux and reboiler ratios.

In one embodiment, a light olefinic fraction comprising ethylene and a heavier olefinic fraction comprising C4 olefins and less than 10 wt % of C5+ hydrocarbon species can be obtained. Preferably also a water-rich fraction is obtained. Also a lighter fraction comprising methane, carbon monoxide, and/or carbon dioxide can be obtained, as well as one or more heavy fractions comprising C5+ hydrocarbons. Such heavy fraction can for example be used as gasoline blending component.

In the process also a significant amount of propylene is normally produced. The propylene can form part of the light olefinic fraction comprising ethene, and which can suitably be further fractionated into various product components. Propylene can also form part of the heavier olefinic fraction comprising C4 olefins. The various fractions and streams referred to herein, in particular the recycle stream, can be obtained by fractionating in various stages, and also by blending streams obtained during the fractionation. Typically, an ethylene and a propylene stream of predetermined purity such as pipeline grade, polymer grade, chemical grade or export quality will be obtained from the process, and also a stream rich in C4 comprising C4 olefins and optionally C4 paraffins. It shall be clear that the heavier olefinic fraction comprising C4 olefins, forming the recycle stream, can be composed from quantities of various fractionation streams. So, for example, some amount of a propylene-rich stream can be blended into a C4 olefin-rich stream. In a particular embodiment at least 90 wt % of the heavier olefinic fraction comprising C4 olefins can be formed by the overhead stream from a debutaniser column receiving the bottom stream from a depropanizer column at their inlet, more in particular at least 99 wt % or substantially all.

Suitably the olefinic reaction effluent comprises less than 10 wt %, preferably less than 5 wt %, more preferably less than 1 wt %, of C6-C8 aromatics. Producing low amounts of aromatics is desired since any production of aromatics consumes oxygenate which is therefore not converted to lower olefins.

According to a second aspect of the invention, there is provided a process for the manufacture of formulated oxygenate conversion catalyst particles suitable to produce an olefinic product, the formulated catalyst particles comprising a combination of at least a molecular sieve having one-dimensional 10 membered ring channels and a matrix, the process comprising adding a Group II metal species to the catalyst particles after the combination of said molecular sieve and the matrix.

Preferably the formulated catalyst manufactured according to the second aspect of the invention is used in the process according to the first aspect of the invention.

The formulated catalyst is preferably produced by spray-drying a slurry of the molecular sieve and matrix then drying and typically calcining. This is especially advantageous for embodiments of the present invention where a further molecular sieve is added to the catalyst, especially when the further molecular sieve has an MFI type framework which helps reduce the proportion of undesired products that lower the selectivity and that may form coke-precursors.

When included, the spray drying step is performed before addition of the group II metal species. When the catalyst particle is dried, ion-exchanged with solution containing ammonium and calcined, the addition of the group II metal species can be performed after drying and ion-exchange of the catalyst particle, but can also be performed after drying, ion-exchange and calcination of the catalyst particle.

The group II metal species preferably comprises calcium. The Group II metal compound may be a metal salt having an anion chosen from the group consisting of acetate, citrate, chloride, perchlorate, nitrate, phosphate; preferably acetate. Typically the group II metal species is water soluble.

After the addition of the group II metal species the catalyst with the group II metal species is normally calcined again.

The Group II metal species will normally undergo a conversion during the subsequent calcination step, e.g. to metal oxide, or metal carbonate, or metal as such, and can remain in substantially this form during subsequent catalyst use. Without wishing to be bound by a hypothesis or theory, it is presently believed that the Group II metal species, be it after such conversion, masks sites on the outer surface of the molecular sieve crystals, which give rise to by-product formation and/or coke formation, especially for embodiments including an MFI type molecular sieve in the formulated catalyst. The group II metal species may also mask such sites giving rise to by-products and/or coke on the binder, particularly when the binder includes kaolin.

The catalyst particles preferably have an average particle size of less than 200 microns, more preferably less than 100 microns.

Any feature of any aspect of any invention or embodiment described herein may be combined with any feature of any aspect of any other invention or embodiment described herein mutatis mutandis.

Embodiments of the invention will now be described by way of example only.

Various spray dried catalysts were prepared by mixing ZSM-23 powder with ZSM-5 powder in various weight ratios, detailed below. In each sample, the sieve fraction used was a 60-80 mesh. The powder mix was added to an aqueous solution and subsequently the slurry was milled. Next, kaolin clay and a silica sol were added and the resulting mixture was spray dried. The catalysts comprised 40 wt % zeolite, 36 wt % kaolin and 24 wt % silica. The spray dried catalysts were exposed to ion-exchange using an ammonium nitrate solution.

For embodiments in accordance with the present invention, calcium was then deposited on the catalyst by means of impregnation using aqueous solutions containing calcium acetate.

During impregnation, a predetermined amount of a solution of the Group II metal species is blended with a predetermined quantity of catalyst. After evaporation of the solvent, a controlled amount of the metal species is left on the catalyst.

The concentration of the solution was adjusted to obtain the appropriate amount of calcium on the different catalysts, as detailed in the tables below. After impregnation the catalysts were dried at 120° C. and were calcined at 600° C. for 2 hours.

Performance evaluation of a first series of catalysts, numbered 1 to 5, is shown in Table 1. The catalysts in Table 1 contain 32 wt % ZSM-23 of SAR 46, 8 wt % ZSM-5 (having a SAR of 280), 24 wt % binder, 36 wt % filler. Catalysts 2-5 contain various amounts of calcium (as detailed in the Table) in accordance with the present invention whereas catalyst 1 does not contain calcium and is included for comparison. The results were obtained under the following test conditions: feed of 3 vol % 1-butene and 6 vol % methanol balanced in N2, temperature 525° C., gas hourly space velocity GHSV of 60,000 ml·$g_{zeolite}^{-1}$·$h^{-1}$ or 24,000 ml·$g_{cat}^{-1}$·$h^{-1}$.

TABLE 1

| | | 1 (Comparative) | | 2 | | 3 | | 4 | | 5 | |
|---|---|---|---|---|---|---|---|---|---|---|---|
| | | \multicolumn{10}{c}{Calcium Content} |
| | | — | | 0.39 wt % | | 0.79 wt % | | 0.94 wt % | | 1.94 wt % | |
| Time (h) | | 0.7 | 5.9 | 0.7 | 5.9 | 0.2 | 5.4 | 0.7 | 5.9 | 0.2 | 5.4 |
| $C2^-/C3^-$ wt-ratio | | 0.26 | 0.14 | 0.18 | 0.13 | 0.14 | 0.11 | 0.11 | 0.09 | 0.11 | 0.09 |
| Methane wt % [i] | | 0.4 | 0.4 | 0 | 0 | 0.5 | 0.3 | 0.3 | 0.3 | 0.5 | 0.3 |
| C2-C5 wt % [i] | | 94.6 | 91.3 | 96.3 | 94.1 | 93.1 | 88.2 | 91.4 | 86.9 | 91.8 | 87.9 |
| C6-C8 wt % [i] [ii] | | 3.7 | 6.7 | 2.9 | 4.9 | 5.4 | 11.3 | 8.1 | 12.5 | 7.6 | 11.8 |

TABLE 1-continued

| | Catalyst sample | | | | | | | | |
|---|---|---|---|---|---|---|---|---|---|
| | 1 (Comparative) | 2 | | 3 | | 4 | | 5 | |
| | | Calcium Content | | | | | | | |
| | — | 0.39 wt % | | 0.79 wt % | | 0.94 wt % | | 1.94 wt % | |
| C6-C8 [i] Aromatics wt % | 1.2 | 1.5 | 0.84 | 1.0 | 1.0 | 0.24 | 0.2 | 0.33 | 0.04 | 0 |
| % C4$_{sats}$ of C4$_{tot}$ start (%) | 6.5 | 9.0 | 3.2 | 4.7 | 4.9 | 7.3 | 4.9 | 7.0 | 2.0 | 3.2 |

[i] wt % of total HC measured in product stream;
[ii] wt % excluding C6-C8 aromatics.

From Table 1, it can be seen that a reduction in aromatics and C4 saturates is observed for the catalysts containing calcium in accordance with the present invention, compared to catalyst 1 which has no calcium. Moreover the C2-C5 olefins yield is at least 70 wt % in all cases, based on total hydrocarbons in the product.

In none of the experiments shown in Table 1 a breakthrough of DME was observed during 15 hours, so all catalysts were stable during this time.

A second series of catalysts, numbered 6 to 8, were prepared containing 37 wt % ZSM-23 and 3 wt % ZSM-5 (having a SAR of 80), 24 wt % binder, 36 wt % filler. The second series of catalysts in Table 2 is different from the first series in Table 1 in that there is a higher content of ZSM-23 compared to ZSM-5 and notably in that the SAR ratio of the ZSM-5 is 80 for the second series compared to 280 for the first series.

Catalyst 6 is a comparative example and contains no calcium, catalysts 7 and 8 contain various amounts of calcium as detailed in Table 2 and are in accordance with the present invention.

The beneficial results for embodiments of the invention are also demonstrated in Table 2, where a reduction in aromatics and C4 saturates is also apparent. A better stability on stream is also achieved. It is thought that this is due to less coke formation, as indicated by the higher C2-C5 production, and a prolonged time-on-stream before DME is present in product stream (see DME breakthrough last row). Indeed, embodiments of the present invention comprising a further molecular sieve with an MFI-type framework, such as ZSM-5, and a low SAR, such as below 100, have been found to produce such results, as detailed in Table 2.

In none of the examples electromagnetic energy was irradiated during any part of the catalyst preparation procedure, or thereafter. In particular no electromagnetic energy with a frequency in the microwave region, more in particular in the range of from about 10 MHz to about 50,000 MHz, was employed. Operating in the absence of such irradiation of electromagnetic energy is clearly preferred, as such irradiation would add much to the complexity of the operation.

Thus the results herein demonstrate that embodiments of the invention improve the performance of oxygenate to olefin catalysts. A particular advantage is the decrease of C4 saturates in the product for a process wherein a C4 olefinic fraction of the product is to be recycled as olefinic co-feed. The lower C4 saturates make thus increases the selectivity of the overall conversion of oxygenate to lower ethylene and/or propylene in such a process.

TABLE 2

| | Catalyst sample | | | | | |
|---|---|---|---|---|---|---|
| | 6 (Comparative) | | 7 | | 8 | |
| | | | Calcium content wt % | | | |
| | untreated | | 0.5 | | 1 | |
| Time (h) | 0.2 | 5.4 | 0.2 | 5.4 | 0.2 | 5.4 |
| C2$^=$/C3$^=$ wt-ratio | 0.28 | 0.15 | 0.22 | 0.15 | 0.14 | 0.11 |
| Methane wt % [i] | 0.6 | 1.0 | 0 | 0.6 | 0.6 | 0.5 |
| C2-C5 wt % [i] | 86.7 | 75.6 | 95.6 | 93.2 | 94.8 | 91.3 |
| C6-C8 wt % [i] [ii] | 8.4 | 19.2 | 3.2 | 5.5 | 3.7 | 8.1 |
| C6-C8 [i] Aromatics wt % | 4.3 | 3.0 | 1.2 | 0.73 | 0.95 | 0.15 |
| % C4$_{sats}$ of C4$_{tot}$ start (%) | 12 | 20.2 | 5.6 | 6.6 | 3.9 | 2.9 |
| DME breakthrough [iii] (h) | 5.4 | | 9 | | >9 | |

[i] wt % of total HC measured in product stream;
[ii] wt % excluding C6-C8 aromatics;
[iii] time at which DME is present in product stream.

What is claimed is:

1. A process for the preparation of an olefinic product, the process comprising reacting an oxygenate feedstock in the presence of formulated oxygenate conversion catalyst particles to produce the olefinic product, the formulated catalyst particles comprising a combination of at least a molecular sieve having one-dimensional 10-membered ring channels and a matrix selected from the group consisting of silica, magnesia, titania, kaolin, montmorillonite and mixtures thereof wherein a Group II metal has been added to the catalyst particles after the combination of said molecular sieve and the matrix wherein the formulated catalyst particles comprise an MFI-type molecular sieve in addition to said molecular sieve, the further molecular sieve having more-dimensional channels, wherein the weight ratio between the molecular sieve and the further molecular sieve is in the range of 1:100 to 100:1 and wherein the silica to alumina (SAR) ratio of the further molecular sieve is less than 150.

2. A process according to claim 1, wherein the Group II metal comprises a metal selected from the group consisting of magnesium, calcium, strontium and barium.

3. A process according to claim 1, wherein the Group II metal is present in an amount of 0.05-10 wt % of the formulated catalyst particles.

4. A process according to claim 1, wherein an external surface area of the catalyst particles is 1-500 m$^2$/g.

5. A process according to claim 1, wherein the oxygenate feedstock is reacted to produce the olefinic product in the presence of an olefinic co-feed.

6. A process according to claim 1, wherein the molecular sieve comprises a TON-type molecular sieve.

7. A process according to claim 1, wherein the molecular sieve comprises an MTT-type molecular sieve.

* * * * *